(12) United States Patent
Jiang et al.

(10) Patent No.: US 8,372,906 B2
(45) Date of Patent: Feb. 12, 2013

(54) HALO-FUNCTIONAL SILANE, PROCESS FOR ITS PREPARATION, RUBBER COMPOSITION CONTAINING SAME AND ARTICLES MANUFACTURED THEREFROM

(75) Inventors: Ping Jiang, New City, NY (US); Eric R. Pohl, Mount Kisco, NY (US); Linda Vecere, Fishkill, NY (US); Juan Alfonso, Hopewell Junction, NY (US)

(73) Assignee: Momentive Performance Materials Inc., Albany, NY (US)

( * ) Notice: Subject to any disclaimer, the term of this patent is extended or adjusted under 35 U.S.C. 154(b) by 26 days.

(21) Appl. No.: 12/881,644

(22) Filed: Sep. 14, 2010

(65) Prior Publication Data

US 2011/0003922 A1 Jan. 6, 2011

Related U.S. Application Data

(63) Continuation of application No. 11/981,371, filed on Oct. 31, 2007, now Pat. No. 7,816,435.

(51) Int. Cl.
*C08K 5/54* (2006.01)
*C07F 7/08* (2006.01)

(52) U.S. Cl. ........................................ 524/263; 556/431

(58) Field of Classification Search ................... 524/263
See application file for complete search history.

(56) References Cited

U.S. PATENT DOCUMENTS

| | | |
|---|---|---|
| 2,811,542 A | 10/1957 | Speier et al. |
| 3,065,254 A | 11/1962 | Silva |
| 3,445,496 A | 5/1969 | Ryan |
| 3,661,954 A | 5/1972 | Legrow |
| 3,692,812 A | 9/1972 | Berger |
| 3,798,196 A | 3/1974 | Rocktaeschel |
| 3,856,756 A | 12/1974 | Wagner et al. |
| 3,869,340 A | 3/1975 | Kotzsch |
| 3,922,436 A | 11/1975 | Bell et al. |
| 3,925,435 A | 12/1975 | Crosby et al. |
| 3,946,059 A | 3/1976 | Janssen et al. |
| 3,956,353 A | 5/1976 | Plueddermann |
| 3,971,883 A | 7/1976 | Meeks et al. |
| 4,044,037 A | 8/1977 | Mui et al. |
| 4,045,459 A | 8/1977 | Foery et al. |
| 4,060,539 A | 11/1977 | Seiler et al. |
| 4,152,347 A | 5/1979 | Pletka et al. |
| 4,290,869 A | 9/1981 | Pigeon et al. |
| 4,574,133 A | 3/1986 | Umpleby |
| 4,595,740 A | 6/1986 | Panster |
| 4,675,426 A | 6/1987 | Crivello |
| 4,820,751 A | 4/1989 | Takeshita |
| 5,116,886 A | 5/1992 | Wolff et al. |
| 5,268,439 A | 12/1993 | Hergenrother et al. |
| 5,326,895 A | 7/1994 | Kubota et al. |
| 5,663,226 A | 9/1997 | Scholl |
| 5,674,932 A | 10/1997 | Agostini |
| 5,821,290 A | 10/1998 | Labauze |
| 5,981,674 A | 11/1999 | Schombourg et al. |
| 6,005,027 A | 12/1999 | Guillet et al. |
| 6,127,468 A | 10/2000 | Cruse |
| 6,172,251 B1 | 1/2001 | Parker |
| 6,204,339 B1 | 3/2001 | Waldman |
| 6,331,605 B1 | 12/2001 | Lunginsland et al. |
| 6,359,046 B1 | 3/2002 | Cruse |
| 6,414,061 B1 | 7/2002 | Cruse |
| 6,528,673 B2 | 3/2003 | Cruse |
| 6,548,594 B2 | 4/2003 | Luginsland |
| 6,608,125 B2 | 8/2003 | Cruse |
| 6,635,700 B2 | 10/2003 | Cruse et al. |
| 6,683,135 B2 | 1/2004 | Cruse |
| 6,777,569 B1 | 8/2004 | Westmeyer |
| 6,849,754 B2 | 2/2005 | Deschler et al. |
| 7,019,074 B2 | 3/2006 | Nakamura et al. |
| 7,074,876 B2 | 7/2006 | Cruse |
| 7,078,551 B2 | 7/2006 | Cruse |
| 7,081,500 B2 | 7/2006 | Cruse |
| 7,122,590 B2 | 10/2006 | Cruse |
| 7,169,872 B2 | 1/2007 | Cruse |
| 7,301,042 B2 | 11/2007 | Cruse |
| 7,326,753 B2 | 2/2008 | Weller |
| 2001/0009966 A1 | 7/2001 | Wunsch |
| 2002/0016487 A1 | 2/2002 | Kayser et al. |
| 2003/0055139 A1 | 3/2003 | Cruse |
| 2003/0130368 A1 | 7/2003 | Luginsland |
| 2003/0199619 A1 | 10/2003 | Cruse |
| 2004/0014840 A1 | 1/2004 | Hong et al. |
| 2005/0009955 A1 | 1/2005 | Cohen et al. |
| 2005/0245753 A1 | 11/2005 | Cruse |
| 2005/0245754 A1 | 11/2005 | Glatzer |
| 2006/0025506 A1 | 2/2006 | Weller |
| 2006/0036034 A1* | 2/2006 | Chaves et al. ................. 525/100 |
| 2006/0041063 A1 | 2/2006 | Cruse |
| 2006/0178487 A1 | 8/2006 | Weller |

(Continued)

FOREIGN PATENT DOCUMENTS

| | | |
|---|---|---|
| DE | 19957325 | 5/2001 |
| DE | 10163945 | 5/2003 |

(Continued)

OTHER PUBLICATIONS

Patterson, et al, "Studies in Macrolide Synthesis: Stereocontrolled Synthesis of a C1-C13 Segment of Concanamycin A" Tetrahedron Letters, Elsevier, Amsterdam, vol. 38, No. 23, 1097, pp. 4183-4186.
Jain, et al. "Application of Chiral (E)-Crotylsilanes in Synthesis: The Asymmetric Synthesis of the C1-C17 Polypropionate Fragment of Rutamycin B" Tetrahedron Letters, Elsevier, Amsterdam, vol. 38, No. 8, 1997, pp. 1345-1348.
Panek, et al. "Total Synthesis of the Action-Depolymerizing Agent (?)-Mycalolide A: Applicationn of Chiral Silane-Based Bond Construction Methodology" Journal of the American Chemical Society, vol. 122, No. 45, 2000, pp. 11090-11097.

*Primary Examiner* — Hui Chin

(74) *Attorney, Agent, or Firm* — Dominick G. Vicari; Joseph S. Ostroff

(57) ABSTRACT

A halo-functional silane possesses halogen functionality and alkanedioxysilyl functionality.

11 Claims, No Drawings

U.S. PATENT DOCUMENTS

| | | |
|---|---|---|
| 2006/0183831 A1 | 8/2006 | Hsu et al. |
| 2006/0183866 A1 | 8/2006 | Pohl |
| 2006/0217474 A1 | 9/2006 | Cruse et al. |
| 2006/0217475 A1 | 9/2006 | Cruse et al. |
| 2006/0281841 A1 | 12/2006 | Weller |
| 2007/0083011 A1 | 4/2007 | Pohl |
| 2007/0185279 A1 | 8/2007 | Cruse |
| 2007/0197725 A1 | 8/2007 | Chaves |
| 2007/0197812 A1 | 8/2007 | Chaves |
| 2007/0197813 A1 | 8/2007 | Chaves |
| 2007/0228322 A1 | 10/2007 | Chaves |
| 2008/0039561 A1 | 2/2008 | Chaves et al. |
| 2008/0039562 A1 | 2/2008 | Chaves et al. |
| 2008/0039644 A1 | 2/2008 | Chaves et al. |
| 2008/0039645 A1 | 2/2008 | Chaves et al. |
| 2008/0194746 A1* | 8/2008 | Jiang et al. .................... 524/261 |

FOREIGN PATENT DOCUMENTS

| | | |
|---|---|---|
| DE | 2050467 | 12/2010 |
| EP | 0068813 | 1/1983 |
| EP | 0097516 | 1/1984 |
| EP | 0211154 | 2/1987 |
| EP | 0396364 | 11/1990 |
| EP | 0631982 | 1/1995 |
| EP | 0631983 | 1/1995 |
| EP | 784072 | 7/1997 |
| EP | 1002835 | 5/2000 |
| EP | 1431275 | 6/2004 |
| FR | 2382456 | 9/1978 |
| GB | 1371804 | 10/1974 |
| GB | 2315688 | 2/1988 |
| JP | 58176538 | 10/1983 |
| JP | 1029385 | 1/1989 |
| JP | 07256474 | 10/1995 |
| JP | 2005232445 | 2/2005 |
| RU | 2123016 | 12/1998 |
| WO | 9909036 | 2/1999 |
| WO | 9920682 | 4/1999 |
| WO | 0149781 | 7/2001 |
| WO | 0222738 | 3/2002 |
| WO | 0248256 | 6/2002 |
| WO | 03/091314 | 11/2003 |
| WO | 2004005395 | 1/2004 |
| WO | 2004037827 | 5/2004 |
| WO | 2004045552 | 6/2004 |
| WO | 2005007660 | 1/2005 |
| WO | 2005040272 | 5/2005 |
| WO | 2006019963 | 2/2006 |
| WO | 2006023785 | 3/2006 |
| WO | 2006023815 | 3/2006 |
| WO | 2007098080 | 8/2007 |
| WO | 2007098121 | 8/2007 |

* cited by examiner

HALO-FUNCTIONAL SILANE, PROCESS FOR ITS PREPARATION, RUBBER COMPOSITION CONTAINING SAME AND ARTICLES MANUFACTURED THEREFROM

CROSS REFERENCE TO RELATED APPLICATIONS

The present application is a continuation of U.S. patent application Ser. No. 11/981,371 filed Oct. 31, 2007, to which priority is claimed and which is herein incorporated by reference in its entirety.

BACKGROUND OF THE INVENTION

This invention relates to halo-functional silanes, their preparation, rubber compositions containing same and articles such as tires manufactured therefrom.

The use of the silica/silane-filler system to reduce the rolling resistance and improve the wet traction of passenger car tires is well known in the art. A reduction of rolling resistance, and therefore less fuel consumption, is also of strong interest for truck tires. However, the use of silica to replace carbon black filler in natural rubber (NR) containing formulations such as truck tread compounds is limited due to poor abrasion resistance. At the present time, truck tire treads use highly reinforcing carbon black for maximum reinforcement and excellent resistance to abrasion. The replacement of carbon black by silica in truck applications has been hampered by ineffective coupling of the silica to the polymer chains of natural rubber.

Polysulfurized alkoxysilanes such as bis(triethoxysilylpropyl)tetrasulfide (TESPT) and blocked mercapto-functional silanes such as 3-octanoylthio-1-propyltriethoxysilane are currently regarded as the most effective and the most widely used coupling agents in rubber compositions for tires, especially those compositions containing styrene-butadiene rubber or butadiene rubber. The reinforcing efficiency and abrasion resistance of vulcanizates filled with silica are not good enough to justify the replacement of carbon black in formulations containing high levels of natural rubber.

The use of non-sulfur silanes is focused on the use of activated double bonds to improve the coupling between fillers and polymer, notably natural rubber. But these non-sulfur coupling agents have shown inadequate coupling performance or performance inferior to that offered by polysulfurized silanes such as bis(triethoxysilylpropyl)tetrasulfide. In addition, the known non-sulfur silanes are very reactive with conventional fillers and elastomers and are therefore difficult to use. When known non-sulfur silanes are used at levels necessary to achieve optimum coupling of filler to the host elastomer, the uncured filled elastomer typically exhibits poorly dispersed filler and short scorch times during curing. Both good filler dispersion and good filler reinforcing efficiency are required to achieve satisfactory end-use properties.

Commonly assigned, copending U.S. patent application Ser. No. 11/703,969, filed Feb. 8, 2007, addresses the inadequate coupling performance of non-sulfur silanes by using halo-functional silane. This halo-functional silane is derived from mono-alcohols that generate volatile organic compound (VOC's) emissions during their use in filled elastomers. The mono-alcohols that are formed during use of the halo-functional silane have low flash points and therefore create potential hazards during fabrication and use. In addition, the mono-alcohol derived halo-functional silanes generate mono-alcohols during use that may impact adversely on the environment.

Glycol derivatives of organosilanes are known in the art. Commonly assigned, copending U.S. patent application Ser. Nos. 11/358,550, filed Feb. 21, 2006, 11/358,818, filed Feb. 21, 2006, 11/358,369, filed Feb. 21, 2006, and 11/358,861, filed Feb. 21, 2006, address the scorch, VOC emissions and coupling performance of filled elastomers by using organofunctional silanes or mixtures of organofunctional silanes that contain both blocked and free mercaptan groups. Commonly assigned, copending U.S. patent application Ser. Nos. 11/505,055, filed Aug. 14, 2006, 11/505,166, filed Aug. 14, 2006, and 11/505,178 filed Aug. 14, 2006, address the scorch, VOC emissions and coupling performance of filled elastomers using organofunctional silanes or mixtures of organofunctional silanes that contain both dispersing and free mercaptan groups. In addition, commonly assigned, copending U.S. patent application Ser. No. 11/104,103, filed Apr. 12, 2005, addresses the VOC emissions of organofunctional silanes containing alkanedioxysilyl groups. The entire contents of aforementioned U.S. patent application Ser. Nos. 11/358,550; 11/358,818; 11/358,681; 11/505,055; 11/505,166; 11/505,178; and 11/104,103 are incorporated by reference herein.

It would be desirable for various rubber applications to have a rubber composition that utilizes increased levels of silica and lower levels of carbon black while maintaining low VOC emissions from the filled elastomeric materials and elastomeric articles during their preparation and use and still exhibiting the properties of low scorch, good filler dispersion and improved abrasion resistance.

SUMMARY OF THE INVENTION

In accordance with the present invention, there is provided a halo-functional silane containing at least one alkanedioxysilyl group.

Further in accordance with the invention, there is provided a process for preparing the aforesaid halo-functional silane which comprises reacting a halo-functional silane derived from mono-alcohol with at least one polyhydroxyl-containing compound and removing by-product mono-alcohol.

Still further in accordance with the invention, there is provided a rubber composition comprising:
 (a) at least one rubber component;
 (b) at least one silane-reactive filler;
 (c) at least one halo-functional silane containing alkanedioxysilyl group; and,
 (d) optionally, at least one activating agent.

The "halo-functional silane" of the present invention is a monomeric, dimeric, oligomeric or polymeric compound possessing halogen functionality and alkanedioxysilyl functionality derived from polyhydroxyl-containing compounds in which the alkanedioxy group is covalently bonded to a single silicon atom through silicon-oxygen bonds to form a ring and/or the alkanedioxy group is covalently bonded to at least two silicon atoms through silicon-oxygen bond to form dimer, oligomer or polymer in which adjacent silyl units are bonded to each other through bridged alkanedialkoxy structure. It is understood that alkanedioxysilyl functionality may contain more than two silicon-oxygen bonds and/or hydroxyl groups that are bonded to the alkanedioxysilyl group through carbon-oxygen bonds.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any numerical range recited herein is intended to include all sub-ranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

DETAILED DESCRIPTION OF THE INVENTION

As previously stated, the halo-functional silane containing at least one alkanedioxysilyl group of this invention provides unique coupling interactions between silane-reactive filler and rubber component and reduces or eliminates the generation of volatile organic compounds.

In accordance with the following embodiments of the halo-functional silane of the invention, the silane may be selected from one or more of general Formulae (1) and/or (2):

$$Y^1(-SiZ^\theta X^1)_a \qquad (1),$$

and $$[Y^1(-SiZ^\theta Z^\beta)_a]_m[Y^1(-SiZ^\beta{}_3)_a]_n[Y^1(-SiZ^\beta{}_2 X^1)_a]_o \\ [[Y^1(-SiZ^\beta{}_2 X^1)_a]_p \qquad (2)$$

wherein:

each occurrence of $Y^1$ is a monovalent or polyvalent halo-containing hydrocarbon group of up to 30 carbon atoms of general Formula (3)

$$[(Z_e CR_{3-e})_b Y^2]_c G^1{}_d \qquad (3)$$

wherein each occurrence of $G^1$ is independently a divalent or polyvalent hydrocarbon group of up to 18 carbon atoms that can optionally contain at least one heteroatom selected from the group consisting of oxygen, sulfur, phosphorous and silicon; each occurrence of $Y^2$ is independently an unsaturated group; each occurrence of Z is independently a halogen atom selected from the groups consisting of F—, Cl—, Br— and I—; and, each occurrence of R is independently selected from the group consisting of hydrogen, alkyl, alkenyl, aryl or aralkyl wherein each R, other than hydrogen, contains up to 30 carbon atoms;

each occurrence of $X^1$ is independently selected from the group consisting of hydrogen, alkyl groups and hydrolyzable groups;

each occurrence of $Z^\beta$, which forms a bridging structure between two different silicon atoms, is [—$OG^2$(OH)$_{f-2}$O—]$_{0.5}$, wherein each occurrence of $G^2$ is independently selected form the group consisting of a hydrocarbylene group of from 2 to 15 carbon atoms or a divalent heterocarbylene group of from 4 to 15 carbon atoms containing one or more etheric oxygen atoms;

each occurrence of $Z^\theta$, which forms a cyclic structure with a silicon atom, is —$OG^2$(OH)$_{f-2}$O—, wherein $G^2$ is independently selected form the group consisting of a hydrocarbylene group of from 2 to 15 carbon atoms or a divalent heterocarbylene group of from 4 to 15 carbon atoms containing one or more etheric oxygen atoms; and, each occurrence of subscripts a, b, c, d, e, f, m, n, o and p is independently an integer where a is 1 to 5; b is 1 to 5; c is 1 to 3, with the proviso that when d is zero, c is 1 and when d is 1, c is from 1 to 3; d is 0 or 1; e is 1 to 3; f is 2 to 6; m is 0 to 20; n is 0 to 18; o is 0 to 20; and, p is 0 to 20, with the proviso that m+n+o+p is equal to or greater than 2.

In connection with the silanes of Formulae (1) and (2), the term "alkyl" includes straight, branched and cyclic alkyl groups; the term "alkenyl" includes any straight, branched, or cyclic alkenyl group containing one or more carbon-carbon double bonds, where the point of substitution can be either at a carbon-carbon double bond or elsewhere in the group; the term "alkynyl" includes any straight, branched or cyclic alkynyl group containing one or more carbon-carbon triple bonds, where the point of substitution can be either at a carbon-carbon triple bond or elsewhere in the group; the term "aryl" includes the non-limiting group of any aromatic hydrocarbon from which one hydrogen atom has been removed; the term "aralkyl" includes, but is not limited to, any of the aforementioned alkyl groups in which one or more hydrogen atoms have been substituted by the same number of like and/or different aryl (as defined herein) substituents. Specific examples of alkyl groups include, but are not limited to, methyl, ethyl, propyl and isobutyl. Specific examples of alkenyl groups include, but are not limited to, vinyl, propenyl, allyl, methallyl, ethylidenyl norbornane, ethylidene norbornyl and ethylidene nororrnenyl. Specific examples of aryl groups include, but are not limited to, tolyl, xylyl, phenyl and naphthalenyl. Specific examples of aralkyl groups include, but are not limited to, benzyl and phenethyl.

In connection with the silanes Formulae (1) and (2), group $X^1$ is selected from the group consisting of hydrogen, alkyl groups and hydrolyzable groups. Some non-limiting representative examples of $X^1$ include methyl, ethyl, propyl, isopropyl, sec-butyl and cyclohexyl; higher straight-chain alkyl such as butyl, hexyl, octyl, lauryl and octadecyl; alkenyl groups such as the non-limiting examples vinyl, allyl, methallyl and 3-butenyl; aryl groups such as the non-limiting examples phenyl and tolyl; aralkyl groups such as the non-limiting examples benzyl and phenethyl; alkoxy groups such as the non-limited examples methoxy, ethoxy, propoxy, isopropoxy, butoxy, phenoxy and benzyloxy; hydroxyl group; halo groups such as the non-limiting examples chloro, bromo and iodo; oximato groups such as the non-limiting examples methylethyloximato, phenylmethyloximato and dimethyloximato; amineoxy groups such as the non-limiting dimethylamineoxy, diethylamineoxy and methylethylamineoxy.

In connection with the structural fragment of Formula (3), group $G^1$ can be any divalent or polyvalent hydrocarbon and can optionally contain at least one heteroatom selected from the group consisting of oxygen, sulfur, phosphorus and silicon atoms. Group $G^1$ can contain up to 18, preferably up to 12, more preferably up to 8 and most preferably up to 4, carbon atoms.

Representative examples of group $G^1$ include, but are not limited to, diethylene cyclohexane; 1,2,4-triethylene cyclohexane; diethylene benzene; phenylene; —$(CH_2)_j$— wherein j is an integer of from 1 to 18, which represent terminal straight-chain alkyls, such as —$CH_2$—, —$CH_2CH_2$—, —$CH_2CH_2CH_2$— and —$CH_2CH_2CH_2CH_2CH_2CH_2CH_2CH_2$—, and their beta-substituted analogs such as —$CH_2(CH_2)_i CH(CH_3)$— wherein i is an integer of from preferably 0 to 15; —$CH_2CH_2C(CH_3)_2CH_2$—; the structure derivable from methallyl chloride, —$CH_2CH(CH_3)CH_2$—; any of the structures derivable from divinylbenzene such as —$CH_2CH_2(C_6H_4)CH_2CH_2$— and —$CH_2CH_2(C_6H_4)CH(CH_3)$— where the notation $C_6H_4$ denotes a disubstituted benzene ring; any of the structures derivable from dipropenylbenzene such as —$CH_2CH(CH_3)$ $(C_6H_4)CH(CH_3)CH_2$— where the notation $C_6H_4$ denotes a disubstituted benzene ring; any of the structures derivable from butadiene such as —$CH_2CH_2CH_2CH_2$—, —$CH_2CH_2CH(CH_3)$— and —$CH_2CH(CH_2CH_3)$—; any of the structures derivable from piperylene such as —CH$_2$CH$_2$CH$_2$CH(CH$_3$)—, —CH$_2$CH$_2$CH(CH$_2$CH$_3$)— and —CH$_2$CH(CH$_2$CH$_2$CH$_3$)—; any of the structures derivable from isoprene such as —CH$_2$CH(CH$_3$)CH$_2$CH$_2$—, —CH$_2$CH$_2$CH(CH$_3$)CH(CH$_3$)—, —CH$_2$C(CH$_3$)(CH$_2$CH$_3$)—, —CH$_2$CH$_2$CH(CH$_3$)CH$_2$—, —CH$_2$CH$_2$C(CH$_3$)$_2$— and —CH$_2$CH[CH(CH$_3$)$_2$]—; any of the isomers of —CH$_2$CH$_2$-norbornyl-, —CH$_2$CH$_2$-cyclohexyl-; any of the diradicals obtainable from norbornane, cyclohexane, cyclopentane, tetrahydrodicyclopentadiene or cyclododecene by loss of two hydrogen atoms; the structures derivable from limonene, —CH$_2$CH(4-CH$_3$-1-C$_6$H$_9$—)CH$_3$, where the notation C$_6$H$_9$ denotes isomers of the trisubstituted cyclohexane ring lacking substitution in the 2 position; any of the monovinyl-containing structures derivable from trivinylcyclohexane such as —CH$_2$CH$_2$ (vinylC$_6$H)CH$_2$CH$_2$— and —CH$_2$CH$_2$ (vinylC$_6$H$_9$)CH(CH$_3$)— where the notation C$_6$H$_9$ denotes any isomer of the trisubstituted cyclohexane ring; any of the monounsaturated structures derivable from myrcene containing a trisubstituted —C═C— such as —CH$_2$CH [CH$_2$CH$_2$CH═C(CH$_3$)$_2$]CH$_2$CH$_2$—, CH$_2$CH [CH$_2$CH$_2$CH═C(CH$_3$)$_2$]CH(CH$_3$)—, —CH$_2$C [CH$_2$CH$_2$CH═C(CH$_3$)$_2$](CH$_2$CH$_3$)—, —CH$_2$CH$_2$CH [CH$_2$CH$_2$CH═C(CH$_3$)$_2$]CH$_2$—, —CH$_2$CH$_2$ (C—)(CH$_3$) [CH$_2$CH$_2$CH═C(CH$_3$)$_2$] and —CH$_2$CH[CH(CH$_3$) (H$_2$CH$_2$CH$_2$═C(CH$_3$)$_2$)]—; any of the monounsaturated structures derivable from myrcene lacking a trisubstituted —C═C— such as —CH$_2$CH(CH═CH$_2$)CH$_2$CH$_2$CH$_2$C (CH$_3$)$_2$—, —CH$_2$CH(CH═CH$_2$)CH$_2$CH$_2$CH[CH (CH$_3$)$_2$]—, —CH$_2$C(═CH—CH$_3$)CH$_2$CH$_2$CH$_2$C(CH$_3$)$_2$—, —CH$_2$C(═CH—CH$_3$)CH$_2$CH$_2$CH[CH(CH$_3$)$_2$]—, —CH$_2$CH$_2$C(═CH$_2$)CH$_2$CH$_2$CH$_2$C(CH$_3$)$_2$—, —CH$_2$CH$_2$C(═CH$_2$)CH$_2$CH$_2$CH[CH(CH$_3$)$_2$]—, —CH$_2$CH═C(CH$_3$)$_2$CH$_2$CH$_2$CH$_2$C(CH$_3$)$_2$— and —CH$_2$CH═C(CH$_3$)$_2$CH$_2$CH$_2$CH[CH(CH$_3$)$_2$]—; and, any of the straight chain or branched alkylenes substituted with at least one heteroatom such as —CH$_2$CH$_2$OCH$_2$—, —CH$_2$CH$_2$ OCH$_2$CH$_2$ OCH$_2$CH$_2$—, —CH$_2$CH$_2$ SCH$_2$CH$_2$ SCH$_2$CH$_2$—, —CH$_2$CH$_2$ Si(CH$_3$)$_2$CH$_2$CH$_2$—.

In connection with the structural fragment of Formula (3), group $Y^2$ therein is a divalent or polyvalent unsaturated hydrocarbon group of from 2 to 12 carbon atoms containing at least one carbon-carbon double bond or at least one carbon-carbon triple bond that of Formula (3). The carbon-carbon double bond or carbon-carbon triple bond can be conjugated or non-conjugated with other carbon-carbon double and/or triple bonds and can include aromatic ring structures. When b in Formula (3) is at least 2, the —CR$_{3-e}$Z$_e$ fragments can be bonded to the same carbon atom on the carbon-carbon double bond, on adjacent carbon atoms of the carbon-carbon double bond or on the carbon atoms of different carbon-carbon bonds. Some non-limiting representative examples of $Y^2$ are alkenylene groups such as —CH═CH—, —CH$_2$CH═CH—, —CH$_2$CH$_2$CH═CH— and —CH$_2$CH═CH—CH═CH— and —CH═C(—)$_2$; alkynylene groups such as —C≡C—, —CH$_2$C≡C— and —CH$_2$CH$_2$C≡C—; and, aromatic groups such as phenylene and 2-methylphenylene.

In structural fragment Formula (3), each occurrence of Z is preferably the halogen atom Cl—.

In structural fragment Formula (3), R is hydrogen; a straight, branched or cyclic alkyl group of up to 30, preferably up to 10, more preferably up to 6, and most preferably up to 3, carbon atoms; a straight, branched or cyclic alkenyl group containing one or more carbon-carbon double bond where the point of substitution can be either at a carbon-carbon double bond or elsewhere in the group and where the alkenyl group contains up to 4, more preferably up to 10, more preferably up to 6, and most preferably up to 3, carbon atoms; and, an aryl group containing up to 30, more preferably up to 20, more preferably up to 12, and most preferably up to 8, carbon atoms.

Representative non-limiting examples of R include alkyl groups such as methyl, ethyl, propyl and isobutyl; alkenyl groups such vinyl, propenyl, allyl, methallyl, ethylidenyl norbornane, ethylidene norbornyl, ethylidenyl norbornene and ethylidene norbornenyl; aryl groups such as phenyl and naphthalenyl; and, aralkyl groups such as benzyl and phenethyl. Some representative non-limiting examples of "cyclic alkyl" and "cyclic alkenyl include norbornyl, norbornenyl, ethylnorbornyl, ethylnorbornenyl, ethylcyclohexyl, ethylcyclohexenyl, cyclohexylcyclohexyl and cyclododecatrienyl.

Representative non-limiting examples of the [—Y(CR$_{3-e}$—Z$_e$)$_b$] moiety of the structural fragment of Formula (3) include —CH═CH—CH$_2$—Cl, —CH═CH—CH (CH$_3$)—Cl, —CH═C(CH$_3$)—CH$_2$—Cl—C—C≡CH$_2$— Cl and —C$_6$H$_4$CH$_2$—Cl where C$_6$H$_4$ represents an divalent substituted benzene ring, —C$_6$H$_4$CH(CH$_3$)—C$_1$-C$_6$H$_4$CH$_2$—Br, —C$_6$H$_4$CHCl$_2$, and —C$_6$H$_4$C$_3$.

In the silanes of Formulae (1) and (2), each occurrence of $X^1$ is $R^1$O— wherein $R^1$ is independently hydrogen, an alkyl group of up to 6, more preferably of up to 3, and more preferably 2, carbon atoms, or $R^2$ which is independently selected from the group consisting of hydrogen and an alkyl group of up to 6, more preferably 1 or 2, and most preferably 1, carbon atom; $G^1$ is independently a hydrocarbon of up to 10, more preferably up to 3, and most preferably 1, carbon atom; each occurrence of R is independently an alkyl group of up to 10 carbons, preferably up to 3, and most preferably 1, carbon atom; each occurrence of $Y^2$ is independently an unsaturated group preferably selected from —CH═CH—, —C≡C— and —C$_6$H$_4$—, more preferably selected from —CH═CH— and —C$_6$H$_4$— and most preferably —C$_6$H$_4$—; each occurrence of Z is Cl— or Br— and preferably is Cl—; and, a, b, c and d are integers in which a is 1; b is 1 or 2; c is 1 or 2; d is 0 or 1; and e is 1 or 2, and preferably a is 1; b is 1; c is 1; d is 1; and e is 1.

Representative non-limiting examples of the halo-functional silane of Formula (1) include: 2-[2-(4-chloromethyl-phenyl)-ethyl]-2,5-dimethyl-[1,3,2]dioxasilinane, 2-[2-(4-chloromethyl-phenyl)-ethyl]-2-methoxy-5-methyl-[1,3,2] dioxasilinane, 2-[2-(4-bromomethyl-phenyl)-ethyl]-2-ethoxy-5-methyl-[1,3,2]dioxasilinane, 2-ethoxy-2-[2-(4-iodomethyl-phenyl)-ethyl]-5-methyl-[1,3,2]dioxasilinane, 2-[2-(4-chloromethyl-phenyl)-ethyl]-2-ethoxy-5-methyl-[1, 3,2]dioxasilinane, 2-[2-(4-chloromethyl-phenyl)-propyl]-2-ethoxy-5-methyl-[1,3,2]dioxasilinane, 2-{2-[4-(1-chloro-ethyl)-phenyl]-propyl}-2-ethoxy-5-methyl-[1,3,2] dioxasilinane, 2-{2-[4-(1-chloro-ethyl)-phenyl]-propyl}-2-ethoxy-4-methyl-[1,3,2]dioxasilinane, 2-[2-(4-chloromethyl-phenyl)-ethyl]-2-ethoxy-4-methyl-[1,3,2] dioxasilinane, 2-[2-(4-chloromethyl-phenyl)-ethyl]-2-ethoxy-4,4,6-trimethyl-[1,3,2]dioxasilinane, 2-[2-(4-chloromethyl-phenyl)-ethyl]-2-ethoxy-[1,3,2]dioxasilinane, 2-[2-(4-chloromethyl-phenyl)-ethyl]-2-ethoxy-[1,3,2]dioxasilolane, 3-{2-[2-(4-chloromethyl-phenyl)-ethyl]-5-methyl-[1,3,2]dioxasilinan-2-yloxy}-2-methyl-propan-1-ol, 3-{2-[2-(3,4-bis-chloromethyl-phenyl)-ethyl]-5-methyl-[1, 3,2]dioxasilinan-2-yloxy}-2-methyl-propan-1-ol, 3-[2-(3-chloro-propenyl)-5-methyl-[1,3,2]dioxasilinan-2-yloxy]-2-methyl-propan-1-ol, 2-(3-chloro-propenyl)-2-ethoxy-5-methyl-[1,3,2]dioxasilinane, 2-(3-chloro-prop-1-ynyl)-2-ethoxy-5-methyl-[1,3,2]dioxasilinane, 2-(3-chloro-prop-1-ynyl)-2-ethoxy-4,4,6-trimethyl-[1,3,2]dioxasilinane, 2-(3- chloro-but-1-ynyl)-2-ethoxy-4,4,6-trimethyl-[1,3,2]
dioxasilinane, 2-[2-(4-chloromethyl-cyclohexyl)-ethyl]-2-
ethoxy-4,4,6-trimethyl-[1,3,2]dioxasilinane, 2-[2-(4-
chloromethyl-cyclohex-3-enyl)-ethyl]-2-ethoxy-4,4,6-
trimethyl-[1,3,2]dioxasilinane, 2-(6-chloro-hex-4-enyl)-2-
ethoxy-5-methyl-[1,3,2]dioxasilinane, 2-(6-chloro-4-
methyl-hex-4-enyl)-2-ethoxy-5-methyl-[1,3,2]
dioxasilinane, {2-[2-(4-chloromethyl-phenyl)-ethyl]-2-
ethoxy-[1,3,2]dioxasilinan-5-yl}-methanol, {2-[2-(4-
chloromethyl-phenyl)-ethyl]-2-ethoxy-5-ethyl-[1,3,2]
dioxasilinan-5-yl}-methanol, and mixtures thereof.

Representative non-limiting examples of the halo-functional silane of Formula (2) include: 2-[2-(4-chloromethyl-phenyl)-ethyl]-2-(3-{2-[2-(4-chloromethyl-phenyl)-ethyl]-[1,3,2]dioxasilinan-2-yloxy}-2-methyl-propoxy)-5-methyl-[1,3,2]dioxasilinane, 2-[2-(4-chloromethyl-phenyl)-ethyl]-2-(3-{2-[2-(4-chloromethyl-phenyl)-ethyl]-5-methyl-[1,3,2]dioxasilinan-2-yloxy}-2-methyl-propoxy)-5-methyl-[1,3,2]dioxasilinane, 2-[2-(4-chloromethyl-phenyl)-ethyl]-2-(3-{2-[2-(4-chloromethyl-phenyl)-ethyl]-4,4,6-trimethyl-[1,3,2]dioxasilinan-2-yloxy}-1,3-dimethyl-butoxy)-4,4,6-trimethyl-[1,3,2]dioxasilinane, 2-[2-(4-chloromethyl-phenyl)-ethyl]-2-(3-{2-[2-(4-chloromethyl-phenyl)-ethyl]-[1,3,2]dioxasilinan-2-yloxy}-1,3-dimethyl-butoxy)-4,4,6-trimethyl-[1,3,2]dioxasilinane, 2-[2-(4-chloromethyl-phenyl)-ethyl]-2-(3-{2-[2-(4-chloromethyl-phenyl)-ethyl]-[1,3,2]dioxasilinan-2-yloxy}-1-methyl-propoxy)-4-methyl-[1,3,2]dioxasilinane, 2-[2-(4-bromomethyl-phenyl)-ethyl]-2-(3-{2-[2-(4-bromomethyl-phenyl)-ethyl]-[1,3,2]dioxasilinan-2-yloxy}-2-methyl-propoxy)-5-methyl-[1,3,2]dioxasilinane, 2-{2-[4-(1-chloro-ethyl)-phenyl]-propyl}-2-[3-(2-{2-[4-(1-chloro-ethyl)-phenyl]-propyl}-[1,3,2]dioxasilinan-2-yloxy)-2-methyl-propoxy]-5-methyl-[1,3,2]dioxasilinane, 2-{2-[4-(1-chloro-ethyl)-phenyl]-propyl}-2-[3-({2-[4-(1-chloro-ethyl)-phenyl]-propyl}-ethoxy-methyl-silanyloxy)-2-methyl-propoxy]-5-methyl-[1,3,2]dioxasilinane, {2-[4-(1-Chloro-ethyl)-phenyl]-propyl}-2-[3-({2-[4-(1-chloro-ethyl)-phenyl]-propyl}-diethoxy-silanyloxy)-2-methyl-propoxy]-5-methyl-[1,3,2]dioxasilinane, 1-[2-({3-[(7-chloro-hept-5-enyl)-diethoxy-silanyloxy]-propoxy}-diethoxy-silanyl)-ethyl]-4-chloromethyl-benzene, 1-[2-({3-[(7-chloro-hept-5-enyl)-ethoxy-methyl-silanyloxy]-propoxy}-ethoxy-methyl-silanyl)-ethyl]-4-chloromethyl-benzene, 1-chloro-7-({3-[(7-chloro-hept-5-enyl)-ethoxy-methyl-silanyloxy]-propoxy}-ethoxy-methyl-silanyl)-hept-2-ene, 3-chloro-1-({3-[(3-chloro-propenyl)-ethoxy-methyl-silanyloxy]-propoxy}-ethoxy-methyl-silanyl)-propene, 3-chloro-1-({3-[(3-chloro-propenyl)-diethoxy-silanyloxy]-propoxy}-diethoxy-silanyl)-propene, 2-(3-Chloro-propenyl)-2-{3-[(3-chloro-propenyl)-ethoxy-methyl-silanyloxy]-2-methyl-propoxy}-5-methyl-[1,3,2]dioxasilinane, 2-(3-chloro-propenyl)-2-{3-[(3-chloro-propenyl)-diethoxy-silanyloxy]-2-methyl-propoxy}-5-methyl-[1,3,2]dioxasilinane, 2-(3-chloro-propenyl)-2-[3-((3-chloro-propenyl)-{3-[(3-chloro-propenyl)-ethoxy-methyl-silanyloxy]-2-methyl-propoxy}-methyl-silanyloxy)-2-methyl-propoxy]-5-methyl-[1,3,2]dioxasilinane, 2-(3-chloro-propenyl)-2-[3-((3-chloro-propenyl)-{3-[(3-chloro-propenyl)-diethoxy-silanyloxy]-2-methyl-propoxy}-ethoxy-silanyloxy)-2-methyl-propoxy]-5-methyl-[1,3,2]dioxasilinane, 2-[2-(4-chloromethyl-phenyl)-ethyl]-2-{3-[[2-(4-chloromethyl-phenyl)-ethyl]-(3-{[2-(4-chloromethyl-phenyl)-ethyl]-ethoxy-methyl-silanyloxy}-2-methyl-propoxy)-methyl-silanyloxy]-2-methyl-propoxy}-5-methyl-[1,3,2]dioxasilinane, 2-[2-(4-chloromethyl-phenyl)-ethyl]-2-{3-[[2-(4-chloromethyl-phenyl)-ethyl]-(3-{[2-(4-chloromethyl-phenyl)-ethyl]-dihoxy-silanyloxy}-2-methyl-propoxy)-ethoxy-silanyloxy]-2-methyl-propoxy}-5-methyl-[1,3,2]dioxasilinane, 2-[2-(4-chloromethyl-phenyl)-ethyl]-2-{3-[[2-(4-chloromethyl-phenyl)-ethyl]-(3-{[2-(4-chloromethyl-phenyl)-ethyl]-ethoxy-methyl-silanyloxy}-1,3-dimethyl-butoxy)-methyl-silanyloxy]-propoxy}-4,4,6-trimethyl-[1,3,2]dioxasilinane, and mixtures thereof.

The halo-functional silane of the present invention includes its partial hydrolyzates. These partial hydrolyzates result when the halo-function silane reacts with water to generate silanols which thereafter condense to form siloxane bonds. The silane hydrolyzates contain at least one $Z^\beta$ group which forms a bridging structure between two different silicon atoms or at least one $Z^\theta$ group which forms a cyclic structure with a silicon atom.

The halo-functional silanes of the invention can be prepared by the process which comprises reacting a halo-functional silane derived from mono-alcohol with at least one polyhydroxyl-containing compound and removing by-product mono-alcohol.

In the case of the halo-functional silanes of Formulae (1) and (2), the foregoing process comprises reacting:

a) at least one halo-functional silane selected from the group consisting of general Formula (4):

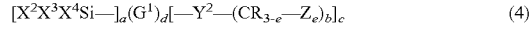

$$[X^2X^3X^4Si-]_a(G^1)_d[-Y^2-(CR_{3-e}-Z_e)_b]_c \qquad (4)$$

wherein:

each occurrence of $X^2$ is independently selected from a hydrolyzable group consisting of Cl—, Br—, I—, $R^1O$—, $R^1(=O)O$—, $R^1{}_2C=NO$— and $R^1{}_2NO$— wherein each $R^1$ is independently selected from the group consisting of hydrogen, alkyl, alkenyl, aryl and aralkyl groups, with each $R^1$, other than hydrogen, containing up to 18 carbon atoms and, optionally, one or more heteroatoms selected from the group consisting of oxygen and sulfur;

each occurrence of $X^3$ and $X^4$ is independently selected from $X^2$ and $R^2$ groups wherein each $R^2$ is independently selected from the group consisting of hydrogen, straight, cyclic or branched alkyl, alkenyl, aryl and aralkyl groups, with each $R^2$, other than hydrogen, containing up to 18 carbon atoms and, optionally, one or more heteroatoms selected from the group consisting of oxygen and sulfur;

each occurrence of $G^1$ is independently a divalent or polyvalent hydrocarbon group of up to 18 carbon atoms optionally containing one or more heteroatoms selected from the group consisting of oxygen, sulfur, phosphorous and silicon;

each occurrence of $Y^2$ is independently an unsaturated group;

each occurrence of Z is independently a halogen atom selected from the group consisting of F—, Cl—, Br— and I—;

each occurrence of R is independently selected from the group consisting of hydrogen, alkyl, alkenyl, aryl or aralkyl, with each R, other than hydrogen, containing up to 30 carbon atoms; and, each occurrence of subscripts a, b, c and d is independently an integer where a is 1 or 5; b is 1 to 5; c is 1 to 3, with the provisos that when d is zero, c is 1 and when d is 1, c is from 1 to 3; d is 0 or 1; and, e is 1 to 3; with b) one or more polyhydroxyl-containing compounds of general Formula (5):

$$G^2(OH)_f \qquad (5)$$

wherein $G^2$ is a hydrocarbyl group of from 2 to 15 carbon atoms or a heterocarbyl group of from 4 to 15 carbon atoms containing one or more etheric oxygen atoms and f is an integer of from 2 to 6, under transesterification reaction conditions, and accompanied by removal of by-product monoalcohol, thereby producing halo-functional silane.

$X^2$ of general Formula (4) is a hydrolyzable group. Some representative non-limiting examples of $X^2$ include alkoxy groups such as ethoxy, ethoxy, propoxy, isopropoxy, butoxy, phenoxy and benzyloxy; hydroxyl group; halo groups such as chloro, bromo and iodo; oximato groups such as methylethyloximato, phenylmethyloximato and dimethyloximato; amineoxy groups such as dimethylaminoxy, diethylaminoxy and methylphenyaminoxy; and, acyloxy groups such as formyloxy, acetoxy and propanoyloxy.

Some representative non-limiting examples of $X^3$ and $X^4$ in Formula (4) include the examples listed above for $X^2$ as well as hydrogen, alkyl groups such as methyl, ethyl, propyl, isopropyl, sec-butyl and cyclohexyl; higher straight-chain alkyl such as butyl, hexyl, octyl, lauryl and octadecyl; alkenyl groups such as vinyl, allyl, methallyl and 3-butenyl; aryl groups such as phenyl and tolyl; and, aralkyl groups such as benzyl and phenethyl The silane(s) of general Formula (4) can, for example, be selected from among the following:
3-chloroprop-1-ynyltriethoxysilane, 3-chloroprop-1-enyltriethoxysilane, 3-chloroprop-1-enyltrimethoxysilane, 3-chloroprop-1-enylmethyldiethoxysilane, 3-chloroprop-1-enyldimethylethoxysilane, 3-chloroprop-1-enyltributoxysilane, 3-bromoprop-1-enyltriethoxysilane, 3-bromoprop-1-enyltrimethoxysilane, 3-bromoprop-1-enyltributoxysilane, 3-iodoprop-1-enyltriethoxysilane, 3-iodoprop-1-enyltrimethoxysilane, 3-iodoprop-1-enyltributoxysilane, (p-chloromethylphenylethyl)triethoxysilane, (p-dichloromethylphenylethyl)triethoxysilane, (p-trichloromethylphenylethyl)triethoxysilane, (p-chloromethylphenylethyl)methyldiethoxysilane, (p-chloromethylphenylethyl)dimethylethoxysilane, (p-α-chloroethylphenylethyl)triethoxysilane, (p-α-chloropropylphenylethyl)triethoxysilane, (p-chloromethylphenylethyl)trimethoxysilane, (p-α-chloroethylphenylethyl)trimethoxysilane, (p-α-chloropropylphenylethyl)trimethoxysilane, (p-chloromethylphenylethyl)tributoxysilane, (p-α-chloroethylphenylethyl)tributoxysilane, (p-α-chloropropylphenylethyl)tributoxysilane, (p-bromomethylphenylethyl)triethoxysilane, (p-α-bromoethylphenylethyl)triethoxysilane, (p-α-bromopropylphenylethyl)triethoxysilane, (p-bromomethylphenylethyl)trimethoxysilane, (p-α-bromoethylphenylethyl)trimethoxysilane, (p-α-bromopropylphenylethyl)trimethoxysilane, (p-bromomethylphenylethyl)tributoxysilane, (p-α-bromoethylphenylethyl)tributoxysilane, (p-α-bromopropylphenylethyl)tributoxysilane, (p-iodomethylphenylethyl)triethoxysilane, (p-α-iodoethylphenylethyl)triethoxysilane, (p-α-iodopropylphenylethyl)triethoxysilane, (p-iodomethylphenylethyl)trimethoxysilane, (p-α-iodoethylphenylethyl)trimethoxysilane, (p-α-iodopropylphenylethyl)trimethoxysilane, (p-iodomethylphenylethyl)tributoxysilane, (p-α-iodoethylphenylethyl)tributoxysilane, (p-α-iodopropylphenylethyl)tributoxysilane. (m-chloromethylphenylethyl)triethoxysilane, (m-α-chloroethylphenylethyl)triethoxysilane, (m-α-chloropropylphenylethyl)triethoxysilane, (m-chloromethylphenylethyl)trimethoxysilane, (m-α-chloroethylphenylethyl)trimethoxysilane, (m-α-chloropropylphenylethyl)trimethoxysilane, (m-chloromethylphenylethyl)tributoxysilane, (m-α-chloroethylphenylethyl)tributoxysilane, (m-α-chloropropylphenylethyl)tributoxysilane, (m-bromomethylphenylethyl)triethoxysilane, (m-α-bromoethylphenylethyl)triethoxysilane, 2,2-bis-(triethoxysilyl)-1-(p-chloromethylphenyl)ethane, 2,3-bis-(triethoxysilyl)-1-(p-chloromethylphenyl)propane, $(CH_3 CH_2O)_3 SiCH_2CH_2CH_2 OCH_2CH=CHCH_2Cl$, and mixtures thereof.

When the silane is a dimer, oligomer, or polymer, each silyl unit thereof is bonded to an adjacent silyl unit through a bridging group resulting from the reaction of the selected silane monomer(s) with one or more polyhydroxyl-containing compounds of aforedescribed general Formula (5).

In one embodiment herein, the selected polyhydrolyx-containing compound of Formula (5) is a diol (glycol) of at least one of the general Formulae (6) and (7):

$$HO(R^0CR^0)_gOH \qquad (6)$$

$$HO(CR^0{}_2CR^0{}_2O)_hH \qquad (7)$$

wherein $R^0$ is independently given by one of the members listed above for R, g is 2 to 15 and h is 2 to 7.

Some representative non-limiting examples of such diols are $HOCH_2CH_2$ OH, $HOCH_2CH_2CH_2$ OH, $HOCH_2CH_2CH_2CH_2$ OH, $HOCH_2CH(CH_3)CH_2$ OH, $(CH_3)_2C(OH)CH_2CH(OH)CH_3$, $CH_3 CH(OH)CH_2CH_2$ OH, diols possessing an etheric oxygen-containing group such as $HOCH_2CH_2$ $OCH_2CH_2$ OH, $HOCH_2CH_2CH_2$ $OCH_2CH_2CH_2$ OH, $HOCH_2CH(CH_3)OCH_2CH(CH_3)OH$, diols possessing a polyether backbone such $HOCH_2CH_2$ $OCH_2CH_2$ $OCH_2CH_2$ OH, and diols of Formula (6) wherein $R^0$ is hydrogen or methyl and e is 3 or 4.

The polyhydroxyl-containing compound of Formula (5) can possess higher hydroxyl functionality such as triols and tetrols. Representative non-limiting examples of such higher hydroxyl functionality compounds include glycerol, trimethylolethane, trimethylolpropane, 1,2,4-butanetriol, 1,2,6-hexanetriol, pentaerythritol, dipentaerythritol, tripentaerythritol, mannitol, galacticol, sorbitol, and combinations thereof. Mixtures of polyhydroxyl-containing compounds of Formulae (5)-(7) can also be used herein.

In accordance with the invention, there is provided a rubber composition comprising:
 (a) at least one rubber component;
 (b) at least one silane-reactive filler;
 (c) at least one halo-functional silane containing at least one alkanedioxysilyl group; and,
 (d) optionally, at least one activating agent.

Halo-functional silane component (c) in the foregoing rubber composition is advantageously one or more of Formulae (1) and/or (2).

The rubber composition herein can optionally contain one or more other hydrolyzable organosilanes that hydrophobate and aid in the dispersion of silane-reactive filler (b). These hydrolyzable organosilanes contain at least one alkyl group, preferably up to 18, and more preferably up to 10, carbon atoms, and at least one $R^3O$— hydrolyzable group wherein $R^3$ is hydrogen or an alkyl, alkenyl, aryl or aralkyl of up to 10 carbon atoms. These hydrolyzable organosilanes can be used, e.g., in amounts of from 0.5 to 10, and preferably from 1 to 5, phr.

In one specific embodiment, the rubber composition herein comprises the mixture and/or reaction product of components (a), (b), (c) and, optionally, (d).

In a further embodiment of the rubber composition herein, halo-functional silane (c) bonds to silane-reactive filler (b) through one functionality and to rubber component (a), e.g., a diene polymer, through a different functionality.

In one embodiment, at least one activating agent (d) can be used in the rubber compounding process to facilitate the coupling reactions between rubber component (a) and halo-functional silane (c). The activating agent can be selected from among the transition metal salts. Useful transition metal salts include metal oxides, metal halides, metal carboxylates, metal hydroxides and other suitable metal complexes. Some representative non-limiting examples of useful transition metal salts include metal oxides such as zinc oxide, aluminum oxide and titanium oxide; metal halides such as zinc chloride, zinc bromide, zinc iodide, aluminum chloride, aluminum bromide, titanium chloride, titanium bromide and stannic chloride; and, metal carboxylates such as zinc stearate, zinc acetate and stannic octanoate.

Rubber component (a) can be one or more diene-based elastomers and/or rubbers and can be selected from any of those that are well known in the art many of which are described in "The Vanderbilt Rubber Handbook", R. F. Ohm, ed.; R.T. Vanderbilt Company, Inc., Norwalk, Conn., 1990 and "Manual For The Rubber Industry", T. Kempermann, S. Koch, J. Sumner, eds.; Bayer AG, Leverkusen, Germany, 1993.

Representative non-limiting examples of rubber component (a) (organic polymers) include natural rubber (NR), synthetic polyisoprene (IR), polybutadiene (BR), various copolymers of butadiene, the various copolymers of isoprene and mixtures of these elastomers; solution styrene-butadiene rubber (SSBR), emulsion styrene-butadiene rubber (ESBR), ethylene-propylene terpolymers (EPDM) and acrylonitrile-butadiene rubber (NBR). Rubber component (a) is preferably natural rubber and/or synthetic polyisoprene.

Suitable monomers for preparing rubber component (a) include conjugated dienes such as isoprene and 1,3-butadiene, and vinyl aromatic compounds such as styrene and alpha methyl styrene, and combinations thereof. In a particular embodiment, rubber component (a) is a sulfur-curable rubber.

Rubber component (a) can be selected from the non-limiting examples of at least one of cis-1,4-polyisoprene rubber (natural and/or synthetic), and preferably natural rubber, emulsion polymerization-prepared styrene/butadiene copolymer rubber, organic solution polymerization-prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (about 35-50 percent vinyl), high vinyl polybutadiene rubber (about 50-75 percent vinyl), styrene/isoprene copolymers, emulsion polymerization-prepared styrene/butadiene/acrylonitrile terpolymer rubber and butadiene/acrylonitrile copolymer rubber. An emulsion polymerization-derived styrene/butadiene (ESBR) is also contemplated as diene-based rubber for use herein such as one having a relatively low to medium styrene content (e.g., from 20 to 29 percent bound styrene) or for some applications, an ESBR having a medium to relatively high bound styrene content (e.g., from 30 to 45 percent bound styrene). In another embodiment, rubber component (a) can be an emulsion polymerization-prepared styrene/butadiene/acrylonitrile terpolymer rubber (e.g., containing from 2 to 40 weight percent bound acrylonitrile).

Suitable solution polymerization-prepared SBR (SSBR) rubbers can contain from 5 to 50, preferably from 9 to 36, and more preferably from 20 to 30, weight percent bound styrene.

In another embodiment, useful polybutadiene elastomers possess a cis-1,4-content of at least 90 weight percent.

In yet another embodiment of the rubber composition of the invention, rubber component (a) is a diene polymer functionalized or modified by an alkoxysilane derivative. Accordingly, silane-functionalized organic solution polymerization-prepared styrene-butadiene rubber and silane-functionalized organic solution polymerization-prepared 1,4-polybutadiene rubbers can be used. These rubber compositions are known, e.g., from U.S. Pat. No. 5,821,290, the entire contents of which are incorporated by reference herein.

In still another embodiment of the rubber composition of the invention, rubber component (a) is a diene polymer functionalized or modified by a tin derivative. Tin-coupled copolymers of styrene and butadiene can be prepared, for example, by introducing a tin coupling agent during the styrene and 1,3-butadiene monomer copolymerization reaction in an organic solvent solution, usually at or near the end of the reaction. Such tin-coupled styrene-butadiene rubbers are well known in the art, e.g., from U.S. Pat. No. 5,268,439, the entire contents of which are incorporated by reference herein. In practice, at least 50 percent, and preferably from 60 to 85 percent, of the tin is bonded to the butadiene units of the styrene-butadiene rubbers to create a tin-dienyl bond.

Silane-reactive filler (b) is a substance that is capable of reaction with silane (c) to form stable Si—O-filler bonds. Silane-reactive filler (b) includes a substance that is added to rubber component (a) to reinforce the cured rubber composition. Reinforcing fillers are materials whose moduli are higher than rubber component (a) of the rubber composition and are capable of absorbing stress from rubber component (a) when this component is strained. Suitable silane-reactive fillers (b) includes fibers, particulates and sheet-like structures and can be made up of inorganic minerals, silicates, silica, clays, ceramics, carbon, organic polymers and diatomaceous earth, and the like. In one embodiment, silane-reactive filler (b) can be a discrete particle or group of particles in the form of aggregates and/or agglomerates. Silane-reactive filler (b) can be mixed with other fillers that do not react with silane (c). These fillers can be used to either extend rubber component (a) or to reinforce the elastomeric network.

Some representative non-limiting examples of suitable silane-reactive fillers (b) include metal oxides such as silica (pyrogenic and/or precipitated), titanium dioxide, aluminosilicate, alumina and siliceous materials such as clays and talc. In one embodiment, particulate precipitated silica is used in connection with a silane. Preferably, silane-reactive filler (b) is a silica used alone or in combination with one or more other fillers. In one embodiment, a combination of silica and carbon black is utilized for a variety of rubber products, e.g., treads for tires. Alumina can be used either alone or in combination with silica. The term "alumina" herein refers to aluminum oxide, or $Al_2O_3$. In a further specific embodiment, the fillers can be hydrated or anhydrous. Use of alumina in rubber compositions is known, e.g., from U.S. Pat. No. 5,116, 886 and EP 631 982, the entire contents of both of which are incorporated by reference herein.

The term "carrier" as used below shall be understood herein to mean a porous or high surface area filler or organic polymer that has a high adsorption or absorption capability and is capable of carrying up to 75 percent liquid silane while maintaining its free-flowing and dry properties. The carrier filler or carrier polymer herein is essentially inert to the silane and is capable of releasing or deabsorbing the liquid silane when added to the elastomeric composition.

Silane-reactive filler (b) herein can be used as a carrier for liquid silanes and reinforcing fillers for elastomers in which halo-functional silane (c) is capable of reacting or bonding with the surface. The fillers that are used as carriers are non-reactive with silane (c). The non-reactive nature of the fillers is demonstrated by the ability of halo-functional silane (c) to be extracted at greater than 50 percent of the loaded silane using an organic solvent. The extraction procedure is described in U.S. Pat. No. 6,005,027, the entire contents of which are incorporated herein by reference.

Representative non-limiting examples of carries include porous organic polymers, carbon black, diatomaceous earth and silicas that are characterized by a relatively low differential of less than 1.3 between the infrared absorbance at 3502 cm$^{-2}$ of the silica when taken at 105° C. and when taken at 500° C. as described in aforementioned U.S. Pat. No. 6,005,027. In one embodiment, the amount of halo-functional silane (c) that can be loaded on the carrier can range from 0.1 to 70 weight percent. In another embodiment, halo-functional silane (c) is loaded onto the carrier at concentrations between about 10 and about 50 weight percent.

Silane-reactive filler (b) includes fillers in which halo-functional silane (c) is reactive with the surface of the filler. Particulate precipitated silica is useful as silane-reactive filler (b), especially when the silica possesses reactive surface silanols. Silane-reactive filler (b) can be provided in hydrated form.

Other fillers that can be mixed with silane-reactive filler (b) include those that are essentially inert to halo-functional silane (c) with which they are admixed as is the case with carbon black and organic polymer fillers.

At least two different silane-reactive fillers can be mixed together and thereafter reacted with silane(s) (c). Thus, one or more carriers possessing metal hydroxyl surface functionality such as the silicas and other siliceous particulates which possess surface silanol functionality can be mixed with one or more reinforcing fillers containing metal hydroxyl surface functionality, e.g., alumina, aluminosilicates, clay, talc, magnesium hydroxide and iron oxide, and thereafter reacted with the selected silane(s) (c).

Precipitated silica is advantageously used as silane-reactive filler (b). Precipitated silica may be characterized as one having a Brunauer, Emmett and Teller (BET) surface area, as measured using nitrogen gas, in a range of from 40 to 600, preferably from 50 to 300, and more preferably from 100 to 150, m$^2$/g. The BET method of measuring surface area is described in the Journal of the American Chemical Society, Volume 60, page 304 (1930) and is the method used herein.

Precipitated silica can also be characterized as one having a dibutylphthalate (DBP) absorption value in a range of from 100 to 350, preferably from 150 to 300, and more preferably from 200 to 250. Silane-reactive fillers (b), as well as the aforesaid alumina and aluminosilicate fillers, typically have a CTAB surface area in a range of from 100 to 220 m$^2$/g. The CTAB surface area is the external surface area as determined by cetyl trimethylammonium bromide with a pH of 9. The method for the measurement of CTAB surface area is described in ASTM D 3849.

The surface area of silane-reactive filler (b) can also be expressed in terms of its mercury porosity surface area as determined by mercury porosimetry. In this technique, mercury is allowed to penetrate the pores of a sample of filler after a thermal treatment to remove volatiles. More specifically, the set-up conditions use a 100 mg sample of filler, remove volatiles therefrom over 2 hours at 105° C. and ambient atmospheric pressure and employ a measurement range of from ambient to 2000 bars pressure. Such measurement can be performed according to the method described in Winslow, et al. in ASTM bulletin, p. 39 (1959) or according to DIN 66133. For such measurement, a CARLO-ERBA Porosimeter 2000 may be used. The average mercury porosity specific surface area for the selected silane-reactive filler (b), e.g., silica, will ordinarily be in a range of from 100 to 300, preferably from 150 to 275, and more preferably from 200 to 250, m$^2$/g.

A suitable pore size distribution for silane-reactive filler (b), e.g., the non-limiting examples of silica, alumina and aluminosilicate,) according to the aforedescribed mercury porisimetry can be as follows: five percent or less of its pores have a diameter of less than 10 nm; from 60 to 90 percent of its pores have a diameter of from 10 to 100 nm; from 10 to 30 percent of its pores have a diameter of from 100 to 1,000 nm; and from 5 to percent of its pores have a diameter of greater than 1,000 nm. Silane-reactive filler (b), e.g., silica, can be expected to have an average ultimate particle size, e.g., in the range of from 0.01 to 0.05 µm as determined by electron microscopy, although the particles can be even smaller, or possibly larger, in size. Various commercially available silicas can used herein such as those available from PPG Industries under the HI-SIL trademark, in particular, HI-SIL 210 and 243; silicas available from Rhone-Poulenc, e.g., ZEOSIL 1165 MP; silicas available from Degussa, e.g., VN2 and VN3, etc., and silicas available from Huber, e.g., HUBERSIL 8745.

Where it is desired for a rubber composition containing both a siliceous filler such as silica, alumina and/or aluminosilicate and a carbon black reinforcing pigment, to be primarily reinforced by the siliceous filler, the weight ratio of siliceous filler to carbon black can be up to 30/1 and, advantageously, is within the range of from 3/1 to 10/1.

Silane-reactive filler (b) can comprise from 15 to 95 weight percent precipitated silica, alumina and/or aluminosilicate and, correspondingly, from 5 to 85 weight percent carbon black having a CTAB value in a range of from 80 to 150. Alternatively, silane-reactive filler (b) can comprise from 60 to 95 weight percent of said silica, alumina and/or aluminosilicate and, correspondingly, from 40 to 5 weight percent of carbon black. The siliceous filler and carbon black, when used together, can be pre-blended or blended together in the manufacture of the vulcanized rubber.

In still another embodiment, there is provided herein a process for preparing a rubber composition comprising mixing components (a), (b), (c) and optionally, (d), in effective amounts. An effective amount of halo-functional silane (c) can range from 0.2 to 20, preferably from 0.5 to 15, and more preferably from 2 to 10, weight percent based on the total weight of the rubber composition. An effective amount of silane-reactive filler (b) can range from 2 to 70, preferably from 5 to 50, and more preferably from 20 to 40, weight percent based on the total weight of the rubber composition. An effective amount of rubber component (a) can range from 30 to 90, preferably from 50 to 95, and more preferably from 60 to 80, weight percent based on the total weight of the rubber composition. The process for preparing the rubber composition can further comprise curing the composition, before, during and/or after its molding. A vulcanized rubber composition should contain a sufficient amount of silane-reactive filler (b) to achieve a reasonably high modulus and high resistance to tear. Specifically, an effective amount of silane-reactive filler (b) can be as low as 5 to 100 parts per hundred parts of rubber (phr) component (a), and preferably from 25 to 85, and more preferably from 50 to 70, phr.

Halo-functional silane (c) can be premixed, or pre-reacted, with particles, aggregates and/or agglomerates of silane-reactive filler (b) or it can be added to the rubber mix during the processing or mixing of rubber (a) and silane-reactive filler (b). If halo-functional silane (c) and silane-reactive filler (b) are added separately to the process mixture during the mixing of rubber component (a) and silane-reactive filler (b), silane (c) can be considered to have coupled in situ to silane-reactive filler (b).

In practice, sulfur-vulcanized rubber products typically are prepared by thermomechanically mixing rubber and various ingredients in a sequentially step-wise manner followed by shaping and curing the compounded rubber to form a vulcanized product. More specifically, first, for the aforesaid mixing of rubber component(s) (a) and various ingredients, typically exclusive of sulfur and sulfur vulcanization accelerators (collectively "curing agents"), the rubber(s) and various rubber compounding ingredients are usually blended in at least one, and optionally two or more, preparatory thermomechanical mixing stage(s) in suitable mixers. Such preparatory mixing is referred to as non-productive mixing or as non-productive mixing steps or stages. Such preparatory mixing is typically conducted at temperatures in the range of from 130° C. to 180° C. and preferably from 140° C. to 160° C.

Subsequent to the preparatory mixing stage, in a final mixing stage, which may also be referred to as a productive mixing stage, curing agents, and, optionally, one or more additional ingredients, are mixed with the rubber compound or composition, typically at a temperature in the range of from 50° C. to 130° C., which is a lower temperature than that utilized in the preparatory mixing stage, in order to prevent or retard premature curing (i.e., "scorching") of the sulfur-curable rubber.

The rubber composition typically is allowed to cool, sometimes after or during a process of intermediate mill mixing, between the aforesaid mixing steps, e.g., to a temperature of 50° C. or lower.

When it is desired to mold and cure the rubber composition, the rubber composition is placed in the desired mold and heated to at least 130° C. and up to 200° C. to bring about the vulcanization of the rubber.

By thermomechanical mixing is meant that the rubber compound, or composition of rubber and rubber compounding ingredients, is mixed in a rubber mixer under high shear conditions where by it autogenously heats up, primarily due to shear and associated friction.

Several chemical reactions can occur at various steps in the mixing and curing processes. For example, the independent addition of a sulfur source can be manipulated by the amount of addition thereof and by sequence of addition relative to the addition of other ingredients to the rubber mixture.

The rubber composition of the invention is advantageously prepared by the process which comprises:

A) thermomechanically mixing in at least one preparatory mixing operation:
  (a) at least one rubber component (a);
  (b) at least one silane-reactive filler (b);
  (c) at least one halo-functional silane (c); and,
  (d) optionally, at least one activating agent (d);
B) blending the mixture resulting from step (A) in a final thermomechanical mixing step, optionally, with at least one curing agent, to provide a substantially uniform mixture; and,
C) optionally curing the mixture resulting from step (B) to provide a cured rubber composition.

In preferred embodiments of the foregoing two-stage process: preparatory mixing step (A) is carried out at a temperature of from 140° C. to 180° C. for from 1 to 20 minutes, and preferably at a temperature of from 150° C. to 170° C. for from 4 to 15 minutes, with 100 parts by weight of sulfur-vulcanizable rubber component (a) selected from the group consisting of conjugated diene homopolymers and copolymers of at least one conjugated diene and aromatic vinyl compound, from 5 to 100, and preferably from to 80, parts by weight of silane-reactive filler (b) containing from 0 to 85 weight percent carbon black, from 0.05 to 20, and preferably, from 2 to 10, parts by weight of halo-functional silane (c) and, optionally, from 0.01 to 15, and preferably from 1 to 5, parts by weight of activating agent (d); final mixing step (B) is carried out with from 0 to parts by weight of at least one curing agent at a temperature of from 50° C. to 130° C. for from 1 to 30, and preferably from 1 to 5, minutes; and, optional curing step (C) is carried out at a temperature of from 130° C. to 200° C. for a period of from 5 to 600, and preferably to 60 minutes.

The rubber composition herein can be compounded by methods known in the rubber compounding art such as mixing component (a) (the various sulfur-vulcanizable constituent rubbers) with various commonly used additive materials such as, for example, curing aids such as sulfur, activators, retarders and accelerators, processing additives such as oils, resins, e.g., tackifying resins, silicas, plasticizers, fillers, pigments, fatty acid, zinc oxide, waxes, antioxidants and antiozonants, peptizing agents, and reinforcing materials such as, e.g., carbon black, and the like. Depending on the intended use of the rubber composition (sulfur-vulcanizable) and cured rubber composition (sulfur-vulcanized material), the aforementioned additives may be selected and used in known and conventional amounts.

Vulcanization can be conducted in the presence of an additional sulfur vulcanizing agent. In one embodiment, some illustrative non-limiting examples of suitable sulfur vulcanizing agents include, e.g., elemental sulfur (free sulfur) or sulfur-donating vulcanizing agents such as amino disulfide, polymeric polysulfide or sulfur-olefin adducts which are conventionally added in the final, i.e., productive, rubber composition mixing step. In another specific embodiment, the sulfur vulcanizing agents (which are common in the art) are used, or added, in the productive mixing stage, in an amount ranging from up to about 8 phr, with a range preferably of from 0.4 to 5 phr, and more preferably of from about 1.5 to about 4.0 phr, and in some cases from about 2 to about 2.5 phr, being generally suitable.

Vulcanization accelerators, i.e., additional sulfur donors, can also be used if desired. Illustrative non-limiting examples of vulcanization accelerators include benzothiazole, alkyl thiuram disulfide, guanidine derivatives and thiocarbamates. Specific accelerators of these types are mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methylpiperazine), dithiobis(N-betahydroxy ethyl piperazine), dithiobis(dibenzyl amine), and combinations thereof. In another embodiment, other additional sulfur donors, include, e.g., thiuram and morpholine derivatives, can be utilized. Representative of such donors are dimorpholine disulfide, dimorpholine tetrasulfide, tetramethyl thiuram tetrasulfide, benzothiazyl-2,N-dithiomorpholide, thioplasts, dipentamethylenethiuram hexasulfide, disulfidecaprolactam, and combinations thereof.

Accelerators can be added to control the time and/or temperature required for vulcanization and to improve the properties of the vulcanizate. A single accelerator system can be used, i.e., a primary accelerator. Conventionally primary accelerator(s) can be used in amounts ranging from 0.5 to 4, and preferably from 0.8 to 1.5 phr. Combinations of a primary and a secondary accelerator can be used with the secondary accelerator being used in smaller amounts, e.g., from 0.05 to 3 phr, in order to activate and to improve the properties of the vulcanizate. Delayed action accelerators and/or vulcanization retarders can also be used.

Suitable types of accelerators include amines, disulfides, guanidines, thioureas, thiazoles, thiurams, sulfenamides, dithiocarbamates, xanthates and combinations thereof. The primary accelerator can be a sulfenamide. If a second accelerator is used, it can be a guanidine, dithiocarbamate or thiuram compound.

Optional tackifier resins can be used at levels of from 0.5 to 10 phr, and preferably from 1 to 5, phr. Typical amounts of processing aids range from 1 to 50 phr. Suitable processing aids can include aromatic, naphthenic and/or paraffinic processing oils and combinations thereof. Typical amounts of antioxidants are from 1 to 5 phr. Representative antioxidants include diphenyl-p-phenylenediamine and others, e.g., those disclosed in the Vanderbilt Rubber Handbook (1978), pages 344-346. Typical amounts of antiozonants are from 1 to 5 phr. Typical amounts of optional fatty acids, e.g., stearic acid, are from 0.5 to 3 phr. Typical amounts of zinc oxide are from 2 to 5 phr. Typical amounts of waxes, e.g., microcrystalline wax, are from 1 to 5 phr. Typical amounts of peptizers, e.g., pentachlorothiophenol, dibenzamidodiphenyl disulfide and combinations thereof, are from 0.1 to 1 phr.

The rubber composition herein can be used for any of a variety of purposes. In one specific embodiment herein, there is provided an article of which at least one component is the herein-described cured rubber composition. In another specific embodiment herein, there is provided a tire at least one component of which, e.g., its tread, comprises the herein-described cured rubber composition. In yet another specific embodiment, the rubber composition herein can be used for the manufacture of such articles as shoe soles, hoses, seals, cable jackets, gaskets or other industrial goods. Such articles can be built, shaped, molded and cured by various known and conventional methods as is readily apparent to those skilled in the art.

The invention can be better understood by reference to the following examples in which the parts and percentages are by weight unless otherwise indicated.

Comparative Example 1

Preparation of 3-chloropropenyltriethoxysilane (Silane A)

A 250 ml 3-neck round-bottom flask was equipped with a reflux condenser, addition funnel and stir bar. Propargyl chloride (50 g, 0.671 mol) and 0.15 g of platinum (±)-1,3-divinyl-1,1,3,3-tetramethyldisiloxane complex (3% by wt. in xylenes) were added to the flask. Triethoxysilane (115.6 g, 0.705 mol) was added dropwise from the addition funnel to the reaction mixture. The flask quickly became warm. After the completion of addition, the flask was kept at 100° C. for one hour. The final product 103 g was purified by distillation (108° C./49 mmHg) as a mixture of isomers. NMR showed a ratio of 1:0.13 of the two isomers.

Comparative Example 2

Preparation of (p-chloromethylphenylethyl)triethoxysilane (Silane B)

A 2-liter 3-neck round-bottom flask was equipped with a reflux condenser, addition funnel and stir bar. Vinylbenzyl chloride (458 g, 3.0 mol), platinum-tetravinyl tetramethylcyclotetrasiloxane complex (0.15 g, 50 ppm Pt) as catalyst, and phenothiazine (0.86 g, 0.1% by wt.) as a promoter were added to the flask. After heating the flask to 70° C., trichlorosilane (406.2 g, 3.0 mol) was added dropwise from the addition funnel to the reaction mixture. After the completion of addition, the flask was kept at around 80° C. for 3 hours. After distillation, the expected hydrosilation product (p-chloromethylphenylethyl)trichlorosilane was obtained and then transesterified with ethanol to produce (p-chloromethylphenylethyl)triethoxysilane (92% yield) as Silane B.

Example 1

Preparation of 2-[2-(4-chloromethyl-phenyl)-ethyl]-2-(3-{2-[2-(4-chloromethyl-phenyl)-ethyl]-[1,3,2] dioxasilinan-2-yloxy}-2-methyl-propoxy)-5-methyl-[1,3,2]dioxasilinane and higher oligomers (Silane C)

A 1 liter round bottom flask fitted with magnetic stirrer, addition funnel, distillation head, 2 thermocouples, receiver and dry ice trap was charged with 100 grams (0.36 moles) of 1-chloromethyl-4-(2-trimethoxysilylethyl)benzene along with 0.099 grams (0.00052 moles) p-toluenesulfonic acid monohydrate. Into the addition funnel was charged 98.3 grams (1.09 moles) 2-methyl-1,3-propanediol. A vacuum pump was connected and the vacuum was lowered while the reaction pot was heated gently (86° C.). To this mixture was added 2-methyl-1,3-propanediol. The mixture was heated for 3 hours 15 minutes and the methanol that was formed during the reaction was removed under reduced pressure resulting in a clear liquid product as silane A. GPC showed the product has a number average molecular weight as 700 (or 800 for weight average molecular weight).

Example 2

Preparation of 2-[2-(4-chloromethyl-phenyl)-ethyl]-2-ethoxy-5-methyl-[1,3,2]dioxansilinane (Silane D)

A 3-neck 250 ml round bottom flask fitted with magnetic stirrer, distillation head, 2 thermocouples, receiver, dry ice trap and vacuum pump was charged with of 1-chloromethyl-4-(2-triethoxysilylethyl)benzene 70.12 grams (0.22 moles) and 19.92 grams of 2-methyl-1,3-propanediol (0.22 moles). Under reduced pressure the reaction pot was slowly heated to a maximum temperature of 80° C. The released ethanol was removed leaving behind a clear liquid product as Silane D.

Example 3

Preparation of 2-(3-chloro-propenyl)-2-ethoxy-5-methyl-[1,3,2]dioxasilinane (Silane E)

A 3-neck 250 ml round bottom flask fitted with magnetic stirrer, distillation head, 2 thermocouples, receiver, dry ice trap and vacuum pump was charged with 46.7 grams (0.20 moles) of 3-chloro-1-propenyltriethoxysilane and 17.8 grams (0.20 moles) 2-methyl-1,3-propanediol. The mixture was heated gently at 55° C. for 2 hours 30 minutes. The ethanol formed during the reaction was removed under reduced pressure resulting in a clear liquid product as Silane E.

Comparative Examples 3, 4 and 5, Examples 4 and 5

Preparation of the Rubber Compositions

In the following examples, the amounts of reactants are parts per hundred of rubber (phr) unless otherwise indicated. The following rubber compositions were prepared based on natural rubber and reinforced with highly dispersible precipitated silica, the said compositions being intended for tread compounds in truck tires. Formulations for the rubber compositions of these examples are described below in Table 1.

The rubber composition of Comp(arative) Ex(ample) 3 contains carbon black as the reinforcing filler. The remaining rubber compositions (Comp. Exs. 4 and 5 and Exs. 4 and 5) contain silica as the reinforcing filler. The silane coupling agents tested are used in equal molar amounts of silicon. The rubber compositions of Comp. Ex. 4 and Exs. 4 and have the same formulations except for the silane component.

TABLE 1

Formulations of the Rubber Compositions

| Component. | Comp. Ex. 3 | Comp. Ex. 4 | Comp. Ex. 5 | Ex. 4 | Ex. 5 |
|---|---|---|---|---|---|
| NR | 100 | 100 | 100 | 100 | 100 |
| Silica | — | 58 | 58 | 58 | 58 |
| CB | 50 | 3 | 3 | 3 | 3 |
| Silane F* | — | 4.4 | — | — | — |
| Silane B (Comp. Ex. 2) | — | — | 5.0 | — | — |
| Silane C (Ex. 1) | — | — | — | 7.0 | — |
| Silane D (Ex. 2) | — | — | — | — | 5.0 |
| Process oil | 5.0 | 5.0 | 5.0 | 5.0 | 5.0 |
| ZnO | 4.0 | 4.0 | 5.0 | 4.0 | 4.0 |
| Stearic Acid | 2.0 | 2.0 | 2.0 | 2.0 | 2.0 |
| 6 PPD | 2.5 | 2.5 | 2.5 | 2.5 | 2.5 |
| Naugurd Q | 2.0 | 2.0 | 2.0 | 2.0 | 2.0 |
| Wax | 1.0 | 1.0 | 1.0 | 1.0 | 1.0 |
| Sulfur | 1.4 | 1.4 | 1.4 | 1.4 | 1.4 |
| TBBS | 1.6 | 1.6 | 1.6 | 1.6 | 1.6 |
| DPG | — | 2.0 | 2.0 | 2.0 | 2.0 |

*Silane F is bis-(3-triethoxysilylpropyl)tetrasulfide, tradename Silquest A-1289 (Momentive Performance Materials)

The notation in Table 1 above is defined as follows: NR: Natural rubber (SMR-L); silica: Zeosil 1165 MP from Rhodia; CB: carbon black (N-220); process oil: Sundex 8125 from Sun Oil; ZnO: Kadox 720C from ZincCorp.; stearic acid: Industrene R from Witco, Crompton; 6 PPD: (Flexzone 7P from Uniroyal); Wax: Sunproof Improved from Uniroyal, Crompton; Nauguard Q: from Uniroyal; Sulfur: Rubbermakers Sulfur 104 from Harwick; TBBS: Delac S from Uniroyal, Crompton; DPG: from Uniroyal, Crompton.

The mixing of the rubber masterbatch was done in a two-pass procedure as hereinafter described using a Krupp mixer with a 1550 cubic centimenter (cc) chamber volume. In the first pass, the mixer was turned on with the mixer at 30 rpm and the cooling water on full. The rubber polymers were added to the mixer and ram down mixed for 60 seconds. Half of the silica and all of the silane with approximately 35-40 grams of this portion of silica in an ethylvinyl acetate (EVA) bag were added and ran down mixed for 60 seconds. The remaining silica and the processing oil in an EVA bag were next added and ram down mixed for 60 seconds. The mixer throat was dusted down, and the mixer's mixing speed was increased to 90 rpm as required to raise the temperature of the rubber masterbatch to 140° C. The master batch was dumped (removed from the mixer), a sheet was formed on a roll mill set at about 60° to 65° C. and the sheet allowed to cool to ambient temperature.

In the second pass, the sheets from the first pass were added to the mixer and ram down mixed for 60 seconds. The rest of the ingredients except for the curatives were added together and ram down mixed for 60 seconds. The mixer throat was dusted down and the mixer's mixing speed was increased to 90 rpm as required to raise the temperature of the rubber master batch to between 135° C. to 140° C. The rubber master batch was mixed for five minutes and the speed of the Krupp mixer as adjusted to maintain the temperature between 135° C. and 140° C.

The rubber masterbatch and the curatives were mixed on a roll mill heated to between 60° C. and 65° C. The sulfur and accelerators were added to the rubber masterbatch and thoroughly mixed on the roll mill and allowed to form a sheet. The sheet was cooled to ambient before curing.

The measurements and tests used to characterize the rubber compositions are described below. The rubber compositions are characterized before and after curing, as indicated below.

The rheological properties of the compositions were measured on a Monsanto R-100 Oscillating Disk Rheometer and a Monsanto M1400 Mooney Viscometer. The specimens for measuring the mechanical properties were cut from 6 mm plaques cured for (t90+1) minutes at 149° C. Curing and testing of the cured rubber compositions in the form of plaques were carried out according to ASTM standards. In addition, small strain dynamic tests were carried out on a Rheometrics Dynamic Analyzer (ARES—Rheometrics Inc.). Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$ and $\tan \delta_{max}$, were extracted from the non-linear responses of the rubber compounds at small strains. In some cases, steady state values of $\tan \delta$ were measured after 15 minutes of dynamic oscillations at strain amplitudes of 35% (at 60° C.). Temperature dependence of dynamic properties was also measured from about −80° C. to +80° C. at small strain amplitudes (1 or 2%) at a frequency of 10 Hz.

The specific curing procedure and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

The specific curing procedure and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

These experimental tests demonstrate the improved (filler/polymer) coupling performances in the rubber compositions of the present invention compared with known rubber compositions such as those using a carbon black filler (Comp. Ex. 3) or a conventional silane coupling agent such as A-1289 (Comp. Ex. 4).

The data for various properties measured before and after curing of the rubber formulations of Table 1 are presented in Tables 2, 3, and 4 below.

TABLE 2

Rheological (Mooney) Properties of the Rubber Compositions

| Mooney Property | Comp. Ex. 3 | Comp. Ex. 4 | Comp. Ex. 5 | Ex. 4 | Ex. 5 |
|---|---|---|---|---|---|
| Viscosity at 100° C. (ML1 + 4) | 53.8 | 37.2 | 44.3 | 41.5 | 42.6 |
| MV at 135° C. (MS1+) | 23.0 | 13.5 | 22.2 | 17.3 | 22.1 |
| Scorch at 135° C. (MS1 + $t_3$) (min) | 3.2 | 6.4 | 17.31 | 8.2 | 15.1 |
| Cure at 135° C. (MS1 + $t_{18}$) (min) | 4.1 | 9.4 | 20.2 | 9.5 | 17.1 |
| Rheometer (ODR) Properties | | | | | |
| $M_H$ (dN-m) (30 min. timer) | 40.3 | 42.1 | 35.3 | 39.5 | 35.9 |
| $M_L$ (dN-m) | 8.0 | 5.1 | 6.5 | 6.5 | 6.0 |
| $M_H - M_L$ | 32.4 | 37.0 | 28.7 | 32.9 | 29.9 |
| t90 (min) (30 min. timer) | 5.8 | 9.7 | 15.1 | 7.8 | 11.7 |
| $t_{s1}$ (min) | 1.9 | 3.3 | 8.1 | 4.0 | 6.9 |

TABLE 3

Physical Properties of the Rubber Compositions

| Physical Property | Comp. Ex. 3 | Comp. Ex. 4 | Comp. Ex. 5 | Ex. 4 | Ex. 5 |
|---|---|---|---|---|---|
| Hardness (Shore A) | 66 | 64 | 61 | 70 | 64 |
| Tensile (MPa) | 27.4 | 29.4 | 30.3 | 28.8 | 28.1 |
| Elongation (%) | 573 | 605 | 528 | 632 | 519 |
| 25% Modulus (MPa) | 1.03 | 1.03 | 0.74 | 1.64 | 0.83 |
| 100% Modulus (MPa) | 2.37 | 2.74 | 2.12 | 2.53 | 2.26 |
| 300% Modulus (MPa) | 11.06 | 12.77 | 14.8 | 10.40 | 13.93 |
| RI (300%/25%) | 10.76 | 12.46 | 20.08 | 6.36 | 16.84 |
| RI (300%/100%) | 4.67 | 4.66 | 6.98 | 4.11 | 6.16 |

TABLE 4

Dynamic Properties of the Rubber Compositions

| Dynamic Property | Comp. Ex. 3 | Comp. Ex. 4 | Comp. Ex. 5 | Ex. 4 | Ex. 5 |
|---|---|---|---|---|---|
| Non-linearity (0-10%) 60° C. | | | | | |
| G'initial (MPa) | 7.15 | 6.9 | 3.86 | 7.99 | 3.63 |
| ΔG' (MPa) | 5.03 | 4.56 | 2.05 | 5.53 | 2.03 |
| G" max (MPa) | 1.1 | 0.72 | 0.349 | 1.24 | 0.368 |
| $\tan\delta_{max}$ | 0.307 | 0.204 | 0.151 | 0.289 | 0.172 |
| Temperature Dependence | | | | | |
| tanδ0° C. | 0.168 | 0.183 | 0.186 | 0.200 | 0.178 |
| G' 0° C. (MPa) | 10.00 | 7.29 | 4.59 | 13.47 | 4.81 |
| G' 60° C. (MPa) | 4.41 | 4.4 | 2.93 | 4.98 | 2.66 |
| tanδ60° C. | 0.241 | 0.154 | 0.112 | 0.233 | 0.133 |

The advantage for reinforcement power obtained with silane (c) in accordance PGP-26T with the invention herein will be readily apparent to those skilled in the art.

Examination of the data presented in Tables 2, 3 and 4 leads to the following observations: the Mooney viscosity values are all low, indicating the good ability of the compositions to be processed in the uncured state and scorching times are long enough to provide a good safety margin.

Compared with the compositions of Comp. Exs. 3 and 4 (the control compositions for carbon black and Silquest A-1289 silane, respectively), those of Ex. 5 have significantly better overall characteristics. In particular, the modulus value under higher deformation (M300) and the (M300/M100) ratio are both appreciably higher for Ex. 5 than for Comp. Exs. 3 and 4 indicating better reinforcement for the former compared with the latter.

The rubber composition of this invention is particularly advantageous for use in the manufacture of tire treads exhibiting low rolling resistance and high wear resistance, especially when the treads are based on natural rubber or synthetic polyisoprene.

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the invention not be limited to any particular exemplary embodiment disclosed herein.

The invention claimed is:

1. A halo-functional silane possessing halogen functionality and alkanedioxysilyl functionality, and partial hydrolyzates thereof, selected from one of general Formulae (1) and (2):

$$Y^1(-SiZ^\theta X^1)_a \quad \quad (1), \text{ and}$$

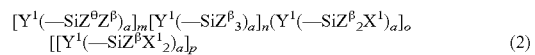

$$[Y^1(-SiZ^\theta Z^\beta)_a]_m[Y^1(-SiZ^\beta_3)_a]_n(Y^1(-SiZ^\beta_2 X^1)_a]_o$$
$$[[Y^1(-SiZ^\beta X^1_2)_a]_p \quad \quad (2)$$

wherein:
each occurrence of $Y^1$ is a monovalent or polyvalent halo-containing hydrocarbon group of up to 30 carbon atoms of general Formula (3):

$$[(Z_e CR_{3-e})_b Y^2]_c G^1_d \quad \quad (3)$$

wherein
each occurrence of $G^1$ is independently a divalent group selected from the group consisting of —$(CH_2)_j$—, where j is an integer from 18, —$CH_2(CH_2)_i CH(CH_3)$—, where i is an integer of from 0 to 15, and —$CH_2 CH(CH_3)CH_2$—;
each occurrence of $Y^2$ is independently an unsaturated group selected from the group consisting of —CH=CH—, phenylene and 2-methyl phenylene;
each occurrence of Z is independently a Cl—,
each occurrence of R is hydrogen;
each occurrence of $X^1$ is independently selected from the group consisting of a methyl, ethyl, propyl, isopropyl, sec-butyl, phenyl, methoxy, ethoxy, propoxy, isopropoxy, butoxy, phenoxy, benzyloxy, and hydroxyl;
each occurrence of $Z^\beta$, which forms a bridging structure between two different silicon atoms, is [—$OG^2$(OH)$_{f-2}$O—]$_{0.5}$, wherein each occurrence of $G^2$ is independently selected from the group consisting of a hydrocarbylene group of from 2 to 15 carbon atoms or a divalent heterocarbylene group of from 4 to 15 carbon atoms containing one or more etheric oxygen atoms;

each occurrence of $Z^\Theta$, which forms a cyclic structure with a silicon atom, is —$OG^2(OH)_{f-2}O$—, wherein $G^2$ is independently selected from the group consisting of a hydrocarbylene group of from 2 to 15 carbon atoms or a divalent heterocarbylene group of from 4 to 15 carbon atoms containing one or more etheric oxygen atoms; and, each occurrence of subscripts a, b, c, d, e, f, m, n, o and p is independently an integer where a is 1; b is 1; c is 1, d is 0 or 1; e is 1; f is 2 to 6; m is 0 to 20; n is 0 to 18; o is 0 to 20; and, p is 0 to 20, with the proviso that m+n+o+p is equal to or greater than 2.

2. The halo-functional silane of claim 1 wherein each occurrence of $X^1$ is independently selected from the group consisting of methyl methoxy, ethoxy, propoxy, isopropoxy, butoxy, hydroxyl, and each occurrence of $G^1$ is independently selected from the group consisting of —$CH_2$—, —$CH_2CH_2$—, —$CH_2CH_2CH_2$—, —$CH_2CH_2CH_2CH_2CH_2CH_2CH_2CH_2$—, and —$CH_2CH(CH_3)CH_2$—.

3. The halo-functional silane of claim 1 wherein $Y^2$ is —CH═CH— or phenylene.

4. The halo-functional silane of claim 3 wherein $Y^2$ is phenylene.

5. A process for preparing the halo-functional silane of claim 1 which comprises reacting:
   a) at least one halo-functional silane selected from the group consisting of general Formula (4):

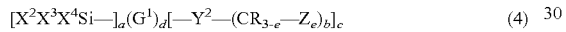

$$[X^2X^3X^4Si—]_a(G^1)_d[—Y^2—(CR_{3-e}—Z_e)_b]_c \quad (4)$$

wherein:
   each occurrence of $X^2$ is independently selected from a hydrolyzable group consisting of Cl—, methoxy, ethoxy, propoxy, isopropoxy, butoxy, phenoxy and benzyloxy;
   each occurrence of $X^3$ and $X^4$ is independently selected from $X^2$, methyl, ethyl, propyl, isopropyl, sec-butyl and phenyl;
   each occurrence of $G^1$ is independently a divalent group selected from the group consisting of —$(CH_2)_j$—, where j is an integer from 18, —$CH_2(CH_2)_iCH(CH_3)$—, where i is an integer of from 0 to 15, and —$CH_2CH(CH_3)CH_2$—;
   each occurrence of $Y^2$ is independently an unsaturated group selected from the group consisting of —CH═CH—, phenylene and 2-methyl phenylene;
   each occurrence of Z is independently a Cl—;
   each occurrence of R is hydrogen; and,
   each occurrence of subscripts a, b, c and d is independently an integer where a is 1; b is 1; c is 1, d is 0 or 1; and, e is 1; with b) one or more polyhydroxyl-containing compounds of general Formula (5):

$$G^2(OH)_f \quad (5)$$

wherein $G^2$ is a hydrocarbyl group of from 2 to 15 carbon atoms or a heterocarbyl group of from 4 to 15 carbon atoms containing one or more etheric oxygen atoms and f is an integer of from 2 to 6, under transesterification reaction conditions, and accompanied by removal of by-product monoalcohol, thereby producing halo-functional silane.

6. A rubber composition comprising:
   (a) at least one rubber component;
   (b) at least one silane-reactive filler;
   (c) at least one silane halo-functional silane possessing halogen functionality and alkanedioxysilyl functionality, and partial hydrolyzates thereof, selected from one of general Formulae (1) and (2):

$$Y^1(—SiZ^\Theta X^1)_n \quad (1), \text{ and}$$

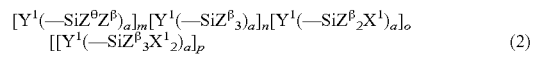

$$[Y^1(—SiZ^\Theta Z^\beta)_a]_m[Y^1(—SiZ^\beta_3)_a]_n[Y^1(—SiZ^\beta_2X^1)_a]_o [[Y^1(—SiZ^\beta_3X^1_2)_a]_p \quad (2)$$

wherein:
   each occurrence of $Y^1$ is a monovalent or polyvalent halo-containing hydrocarbon group of up to 30 carbon atoms of general Formula (3):

$$[(Z_eCR_{3-e})_bY^2]_cG^1_d \quad (3)$$

wherein
   each occurrence of $G^1$ is independently a divalent group selected from the group consisting of —$(CH_2)_j$—, where j is an integer from 18, —$CH_2(CH_2)_iCH(CH_3)$—, where i is an integer of from 0 to 15, and —$CH_2CH(CH_3)CH_2$—;
   each occurrence of $Y^2$ is independently an unsaturated group selected from the group consisting of —CH═CH—, —C≡C—, phenylene and 2-methyl phenylene;
   each occurrence of Z is independently a Cl—; and,
   each occurrence of R is hydrogen;
   each occurrence of $X^1$ is independently selected from the group consisting of a methyl, ethyl, propyl, isopropyl, sec-butyl, phenyl, methoxy, ethoxy, propoxy, isopropoxy, butoxy, phenoxy, benzyloxy, and hydroxyl;
   each occurrence of $Z^\beta$, which forms a bridging structure between two different silicon atoms, is [—$OG^2(OH)_{f-2}O$—]$_{0.5}$, wherein each occurrence of $G^2$ is independently selected from the group consisting of a hydrocarbylene group of from 2 to 15 carbon atoms or a divalent heterocarbylene group of from 4 to 15 carbon atoms containing one or more etheric oxygen atoms;
   each occurrence of $Z^\Theta$, which forms a cyclic structure with a silicon atom, is —$OG^2(OH)_{f-2}O$—, wherein $G^2$ is independently selected from the group consisting of a hydrocarbylene group of from 2 to 15 carbon atoms or a divalent heterocarbylene group of from 4 to 15 carbon atoms containing one or more etheric oxygen atoms; and,
   each occurrence of subscripts a, b, c, d, e, f, m, n, o and p is independently an integer where a is 1; b is 1; c is 1, d is 0 or 1; e is 1; f is 2 to 6; m is 0 to 20; n is 0 to 18; o is 0 to 20; and, p is 0 to 20, with the proviso that m+n+o+p is equal to or greater than 2, and,
   (d) optionally, at least one activating agent.

7. The rubber composition of claim 6, wherein $Y^2$ is —CH═CH— or phenylene that is bonded to the —$CR_{3-e}Z_e$ fragment or at least one carbon-carbon triple bond that is bonded to the —$CR_{3-e}Z_e$ fragment.

8. The cured rubber composition of claim 6.

9. The cured rubber composition of claim 8 which is a tire, a tire component, a shoe sole, a hose, a seal, a cable jacket, a gasket or an industrial good.

10. A composition comprising:
   (a) a silane-reactive filler; and
   (b) at least one halo-functional silane possessing halogen functionality and alkanedioxysilyl functionality, and partial hydrolyzates thereof, selected from one of general Formulae (1) and (2):

$$Y^1(—SiZ^\Theta X^1)_a \quad (1), \text{ and}$$

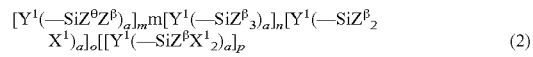

$$[Y^1(—SiZ^\Theta Z^\beta)_a]_m[Y^1(—SiZ^\beta_3)_a]_n[Y^1(—SiZ^\beta_2 X^1)_a]_o[[Y^1(—SiZ^\beta X^1_2)_a]_p \quad (2)$$

wherein:
each occurrence of $Y^1$ is a monovalent or polyvalent halo-containing hydrocarbon group of up to 30 carbon atoms of general Formula (3):

$$[(Z_e CR_{3-e})_b Y^2]_c G^1_d \qquad (3)$$

wherein
each occurrence of $G^1$ is independently a divalent group selected from the group consisting of $-(CH_2)_j-$, where j is an integer from 18, $-CH_2(CH_2)_i CH(CH_3)-$, where i is an integer of from 0 to 15, and $-CH_2CH(CH_3)CH_2-$;
each occurrence of $Y^2$ is independently an unsaturated group selected from the group consisting of $-CH=CH-$, $-C\equiv C-$, phenylene and 2-methyl phenylene;
each occurrence of Z is independently a Cl—; and,
each occurrence of R is hydrogen;
each occurrence of $X^1$ is independently selected from the group consisting of a methyl, ethyl, propyl, isopropyl, sec-butyl, phenyl, methoxy, ethoxy, propoxy, isopropoxy, butoxy, phenoxy, benzyloxy, and a hydroxyl;
each occurrence of $Z^\beta$, which forms a bridging structure between two different silicon atoms, is $[-OG^2(OH)_{f-2}O-]_{0.5}$, wherein each occurrence of $G^2$ is independently selected from the group consisting of a hydrocarbylene group of from 2 to 15 carbon atoms or a divalent heterocarbylene group of from 4 to 15 carbon atoms containing one or more etheric oxygen atoms;
each occurrence of $Z^\Theta$, which forms a cyclic structure with a silicon atom, is $-OG^2(OH)_{f-2}O-$, wherein $G^2$ is independently selected from the group consisting of a hydrocarbylene group of from 2 to 15 carbon atoms or a divalent heterocarbylene group of from 4 to 15 carbon atoms containing one or more etheric oxygen atoms; and,
each occurrence of subscripts a, b, c, d, e, f, m, n, o and p is independently an integer where a is 1; b is 1; c is 1, d is 0 or 1; e is 1; f is 2 to 6; m is 0 to 20; n is 0 to 18; o is 0 to 20; and, p is 0 to 20, with the proviso that m+n+o+p is equal to or greater than 2.

11. The composition of claim 10, wherein the silane-reactive filler (a) is at least one selected from the group consisting of silica, titanium dioxide, aluminosilicate, alumina and siliceous materials, and combination thereof.

* * * * *